(12) United States Patent
Harman

(10) Patent No.: US 6,459,446 B1
(45) Date of Patent: Oct. 1, 2002

(54) EYE TRACKING APPARATUS

(75) Inventor: Philip Victor Harman, Scarborough (AU)

(73) Assignee: Dynamic Digital Depth Research Pty. Ltd., Bentley (AU)

( * ) Notice: Subject to any disclaimer, the term of this patent is extended or adjusted under 35 U.S.C. 154(b) by 0 days.

(21) Appl. No.: 10/077,953

(22) Filed: Feb. 20, 2002

Related U.S. Application Data

(62) Division of application No. 09/574,975, filed as application No. PCT/AU98/00969 on Nov. 20, 1998.

(30) Foreign Application Priority Data

Nov. 21, 1997 (AU) .............................................. PP0480

(51) Int. Cl.[7] .......................... H04N 15/00; H04N 13/04
(52) U.S. Cl. .............................. 348/51; 348/42; 348/53
(58) Field of Search .............................. 348/42, 51, 53, 348/56, 59, 169; 382/154; 359/376, 462; 342/180; 345/6, 419

(56) References Cited

U.S. PATENT DOCUMENTS

| | | | |
|---|---|---|---|
| 5,070,883 A | | 12/1991 | Kasahara |
| 5,231,674 A | | 7/1993 | Cleveland et al. |
| 5,311,220 A | * | 5/1994 | Eichenlaub .................. 348/55 |
| 5,349,379 A | * | 9/1994 | Eichenlaub .................. 348/59 |
| 5,365,370 A | | 11/1994 | Hudgins |
| 5,546,120 A | * | 8/1996 | Miller et al. ................. 348/59 |
| 5,777,720 A | * | 7/1998 | Shapiro et al. .............. 351/237 |
| 5,953,156 A | * | 9/1999 | Muench ...................... 359/464 |
| 5,978,143 A | * | 11/1999 | Spruck ........................ 359/619 |
| 6,008,484 A | * | 12/1999 | Woodgate et al. ......... 250/201.1 |
| 6,075,557 A | * | 6/2000 | Holliman et al. ............ 348/51 |
| 6,101,008 A | * | 8/2000 | Popovich ..................... 351/237 |
| 6,163,336 A | * | 12/2000 | Richards ...................... 348/42 |
| 6,175,431 B1 | * | 1/2001 | Waldern et al. .............. 359/15 |
| 6,224,214 B1 | * | 5/2001 | Martin et al. .................. 353/7 |

FOREIGN PATENT DOCUMENTS

| | | |
|---|---|---|
| JP | 1-259347 | 10/1989 |
| JP | 1-259348 | 10/1989 |
| JP | 1-259349 | 10/1989 |
| WO | WO 96/18925 | 6/1996 |

* cited by examiner

*Primary Examiner*—Vu Le
(74) *Attorney, Agent, or Firm*—Banner & Witcoff, Ltd.

(57) ABSTRACT

A tracking system is provided for locating the eyes of a viewer including: an illumination element; a plurality of cameras; and a processor; wherein at least the viewer's eyes are illuminated by the illumination element to enable capture by each camera, and wherein the processor is adapted to process images from each camera so as to detect the position of the viewer's eyes.

9 Claims, 9 Drawing Sheets

EYE TRACKING APPARATUS

CROSS-REFERENCE TO RELATED APPLICATIONS

This application is a divisional of U.S. patent application Ser. No. 09/574,975, filed May 19, 2000, which is a continuation of International Application No. PCT/AU98/00969 (published as WO 99/27412), filed Nov. 20, 1998 and designating the United States, which is based upon and claims the benefit of priority from the prior Australian Application No. PP 0480, filed Nov. 21, 1997, the entire contents of which are incorporated herein by reference.

FIELD OF THE INVENTION

The present invention is directed towards an improved eye tracking apparatus, and in particular an eye tracking apparatus for use on an auto stereoscopic viewing system.

BACKGROUND ART

The present Applicant's original 3-D auto stereoscopic display unit included an eye tracking unit to enable the correct positioning of a stereoscopic projector pair, to thereby enable the observer to view 3-D video without the use of special glasses. This tracking system, which was disclosed in Australian Application No. 42929/96, required the data for the location of eyes in the x and y directions. That is, the horizontal and the vertical positions of the eyes from a known datum point at a set distance from the single camera.

The earlier developments were based on the premise that the viewer would be located a relative fixed distance from the screen. However, it is now desirable to develop a system which is able to determine the location of the eyes in the x, y and z directions. That is, the horizontal (lateral) position, vertical (height) position and horizontal (depth) position from a known datum point. Such a system will enable an observer to move left and right, up and down, and also forwards and backwards with respect to the screen. However, to create such a system additional data is required in order to obtain the depth or z information.

The present applicants have investigated a number of alternative systems using feed back focus information and ultrasonics. However these other methods have not been found to be technically or commercially practical at this time.

SUMMARY OF THE INVENTION

It is therefore the object of the present invention to provide an eye tracking system which is capable of providing the location of the observer's eyes in the x, y and z directions.

It is also intended that the observer should not be required to wear any specific head-gear and the system should track the observer reliably irrespective of any corrective glasses worn by the observer. Preferably, the system should correctly report the observer's eye position during momentary blinking or periods where one or both of the observer's eyes are closed or the viewer has momentarily looked away from the system. Ideally, it is also intended that the system should reliably differentiate between the observer's eyes and other facial features e.g., earrings or background objects.

With the above object in mind the present invention provides in one aspect a tracking system for locating the head and/or eyes of a viewer including an illumination means; a plurality of cameras; and a processing means; wherein at least one of the viewer's eyes is illuminated by the illumination means to enable capture by each camera, and said processing means is adapted to process images from each camera so as to detect the position of the viewer's eyes and/or head.

For a system that is required to track in the z direction as well as x and y then preferably two cameras can be located on either side of the observers head or the autostereoscopic display system that requires the coordinates of the observer to be determined. The processing means is then able to utilize a method of triangulation to locate the viewer's head and/or eyes. In order to obtain a more compact tracking system, each camera can be associated with a corresponding mirror ideally located at 135 relative to the optical axis of each respective camera. The addition of such mirrors does not adversely affect the performance of each camera, but do allow for a more compact system.

Ideally, the illumination means can be formed from a plurality of separate illumination means, each separate illumination means being moveable in response to movement of the viewer.

It will be understood that such illumination means will conform to local safety regulations.

In a further aspect the present invention provides a tracking tower for locating the eyes of a viewer including:
  an illumination means for illuminating at least the eyes of a viewer;
  a vertically mounted camera for capturing at least the reflected light from the eyes of the viewer; and
  a mirror positioned to enable the vertically mounted camera to capture images in front of the tracking tower.

In yet a further aspect the present invention provides a method of tracking the eyes of a viewer including:
  projecting light capable of being reflected from the cornea of a viewer from an illumination means onto the eyes of the viewer;
  capturing the image of the viewer by a plurality of cameras capable of detecting the reflected light from the viewer's cornea;
  and processing the captured images from each camera in a processing means to determine the position of the viewer's eyes.

In another aspect the present invention provides an autostereoscopic display system including:
  a display means for displaying images to be viewed by a viewer;
  a tracking tower located on either side of the display means, each tracking tower including:
    an upper and lower illumination means for illuminating at least the eyes of a viewer;
    a vertically mounted camera for capturing at least the reflected light from the eyes of the viewer; and
    a mirror positioned to enable the vertically mounted camera to capture images of the viewer in front of the tracking tower;
  a processing means located below the display means for receiving the images captured by each camera, determining the position of the viewers eyes, and sending the output from the processing means to each tracking tower to thereby adjust each said camera in response to movement of the viewer;
  and wherein the output from the processing means is utilized to display respective left and right eye images of the image to be viewed by the viewer on the display means.

DETAILED DESCRIPTION

Figure 1:
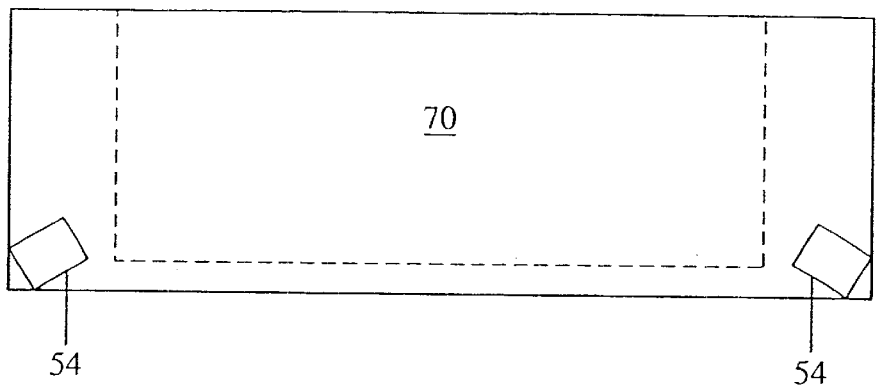
FIG. 1 shows a preferred set-out of the present invention.
Figure 1:
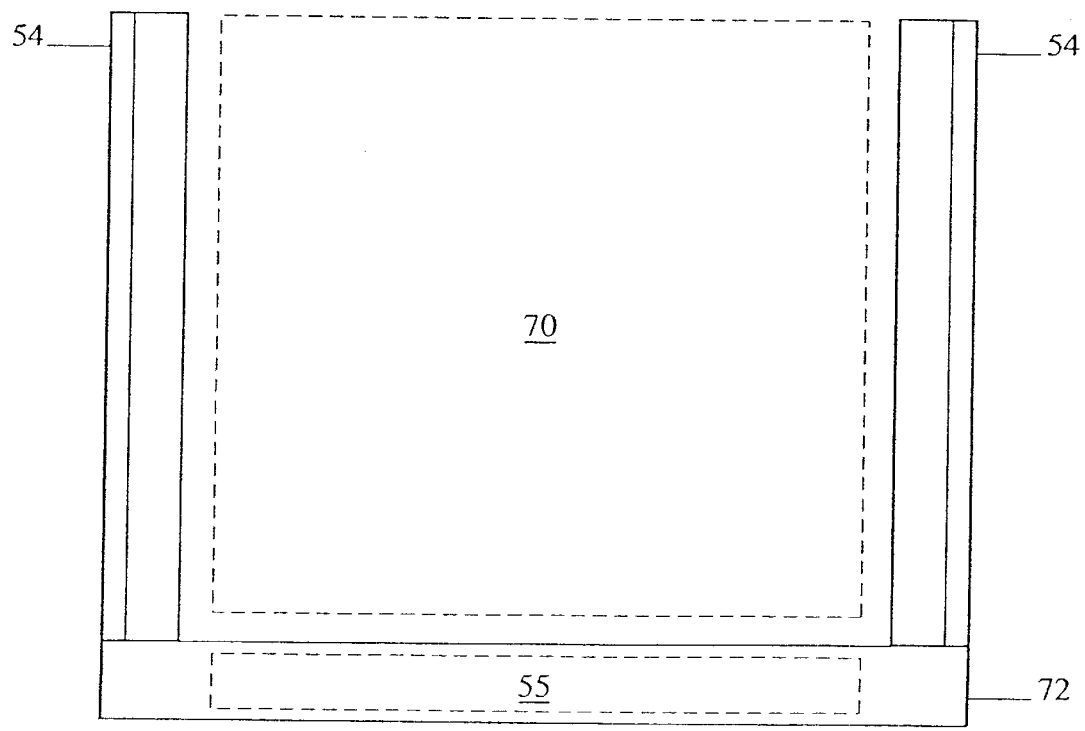

In order that the system should reliably track the eyes of an observer, under standard domestic and industrial ambient lighting conditions, it was necessary to determine the optimum manner in which the observers face should be illuminated so as to maximize the uniqueness of the reflections from the observers eyes and minimize the occurrence of other reflections that could be mistaken as eye reflections.

Through experimentation it was discovered that a localized source of light shone into the face of an observer returned a high level of reflection of that source from the cornea of the observers eyes. In viewing these cornea reflections it was observed that the characteristics of such reflections were sufficiently unique to enable them to be reliably differentiated from other reflections from the observers face, and also other objects within the vicinity of the observer.

In order to prevent discomfort to the viewer, a source of non-visible light is desirable and infrared is a preferred solution.

However, should the observer be wearing corrective glasses, it was determined that reflections from the cornea may not be detectable through the glasses, or may be difficult to differentiate from reflections of the illuminating light source from the observers glasses.

Under these circumstances, it was noted that the reflections from the outside rim of the glasses were sufficiently unique to enable them to be reliably differentiated from other reflections from the observers face and other objects within the vicinity of the observer.

Since the general shape of glasses are well known, it is possible to determine the left, right, upper and lower boundaries of the observers glasses and from this rectangle estimate the x and y coordinates of the observers eye(s).

If the x and y coordinates of the observers eyes or glass rims, in relation to some fixed datum, are to be located then illuminating the observers face with a localized source of infrared light and imaging the viewers face with a video camera sensitive to infrared light will enable the use of computer image processing techniques to determine these coordinates. This is a preferred embodiment of the current invention.

Since general eye and glasses characteristics are generally consistent between observers, computer image processing techniques can take advantage of these characteristics and use them to distinguish between wanted and unwanted reflections.

Should the distance z of the observer from a fixed datum also be required then two such configurations can be placed a known distance apart, and in the preferred embodiment, either side of the viewers face or autostereoscopic display device, and standard triangulation techniques applied to determine the z distance of the observer from the datum.

This configuration will enable the eyes or glasses of the observer to be tracked within a volume determined by the characteristics of the lens of the video camera used. Whilst a wide angle lens could be used to provide a large tracking area, this will also image objects other than the observer's face which could result in extraneous objects being incorrectly interpreted as eyes, thus reducing the reliability of the tracking system.

In order to increase the reliability of eye tracking it is desirable that the video camera should utilize a narrow angle lens, such that only the observer's eyes are imaged and other extraneous objects are eliminated.

However, such a configuration may yield an unacceptably small volume within which the observer's eyes can be successfully tracked.

In order to increase the tracking volume, without reducing the reliability of the system, the video camera(s) can pan and tilt so as to follow the observer's movements. This can be achieved since, once the initial location of the observers eyes have been determined, the x and y coordinates so obtained can be used as the input of a pan and tilt control system that keeps the observers eyes within the field of view of the video camera(s). Should the location of the viewers eyes be lost then after a predetermined period the control system would return the camera to a known home position.

Additionally, once the viewer's eyes have been located the characteristics of the lens of the video camera can be altered, by the use of a power zoom for example, to optimize the image size as the position of the observer changes in the z axis.

In more detail, the preferred embodiment of the present invention involves the use of two horizontally mounted cameras fitted with power pan, tilt, zoom and focus. Alternatively, for functional compactness the cameras can be mounted vertically and use a mirror oriented at 45° to the horizontal, to obtain the correct field of view. It will be appreciated that a camera would normally be horizontally mounted. If space constraints require the camera to be mounted vertically, the mirror will be required to correct the optical path of the camera. Further, the camera need not be vertically mounted at 90°, but rather may be at any angle convenient to the particular application provided that the orientation of the mirror is adjusted to provide the correct optical path for the camera. This mirror may be fixed, therefore giving no tilt function or, articulated to achieve the tilt function. The independent data derived from both cameras can be processed through triangulation to find the x, y and z depth data.

Preferably, the illumination means includes infra red (IR). In order that the system will operate within the safety requirements for IR illumination, a camera with high sensitivity in the IR region is required. The functional requirement of the camera is to capture the reflected light from the viewer's cornea, or rim of corrective glasses if worn. Ideally, the reflected IR light is captured over two or three pixels of the camera's CCD element. This interpolates to the camera's field of view, at the greater viewing range, to span approximately 1½ head widths. The three dimensional space detailed by x, y and z as a region in which eye tracking is effective, will be referred to as the zone of regard. In order to achieve the inspection of, or to scan the zone of regard, the camera needs to pan horizontally.

As previously indicated the safe usage of the equipment is a primary design requirement in order to conform to respective IR safety regulations. For example, in Australia the IR illumination level must be below the Class 1 IR Illumination Standards Requirement. This IR illumination level must also be safe for the casual observer and not only the primary viewer. That is, the IR illumination level must be safe for both the primary viewer, and also for any person who may come within the illuminated region. In order to further reduce the mean level of IR the observer, or other person in the vicinity of the system, is exposed to, the IR illumination source may be pulsed rather than permanently illuminated. In the preferred embodiment the IR source would be turned on for a period during which the shutter of the CCD video camera is open.

As a further means of reducing the level of IR radiation the observer is exposed to, the on time of the illumination source can be varied. Since the distance of the observer from the system is known, the length of time the IR illumination is on can be altered in relation to the distance the viewer is from the IR source. Since less illumination is required the closer the observer is to the illumination source, as the observer moves closer to the system the on time can be reduced and visa versa.

Should the shutter speed of the CCD camera be altered in accordance with the distance of the observer from the camera, or other parameters, then the on time of the IR source may be varied accordingly.

Preferably, the cameras are equipped with a pan mechanism in order to increase the horizontal field of view of the eye tracker system. Accordingly, in order to accommodate the pan movement requirement, the illumination means (61a and 61b) is ideally coaxially articulated in the direction of the camera so as to further assist in minimizing illumination energy and satisfying IR illumination Safety Standards. It will be understood that the illumination means need not be formed by an upper and lower illumination means, but could be formed by a single illumination means, or other functionally equivalent arrangement. In another preferred embodiment the illumination sources are located close to the viewers face, in order to maximize the incident IR radiation on the face of the observer, and the cameras located some distance behind.

Figure 2:
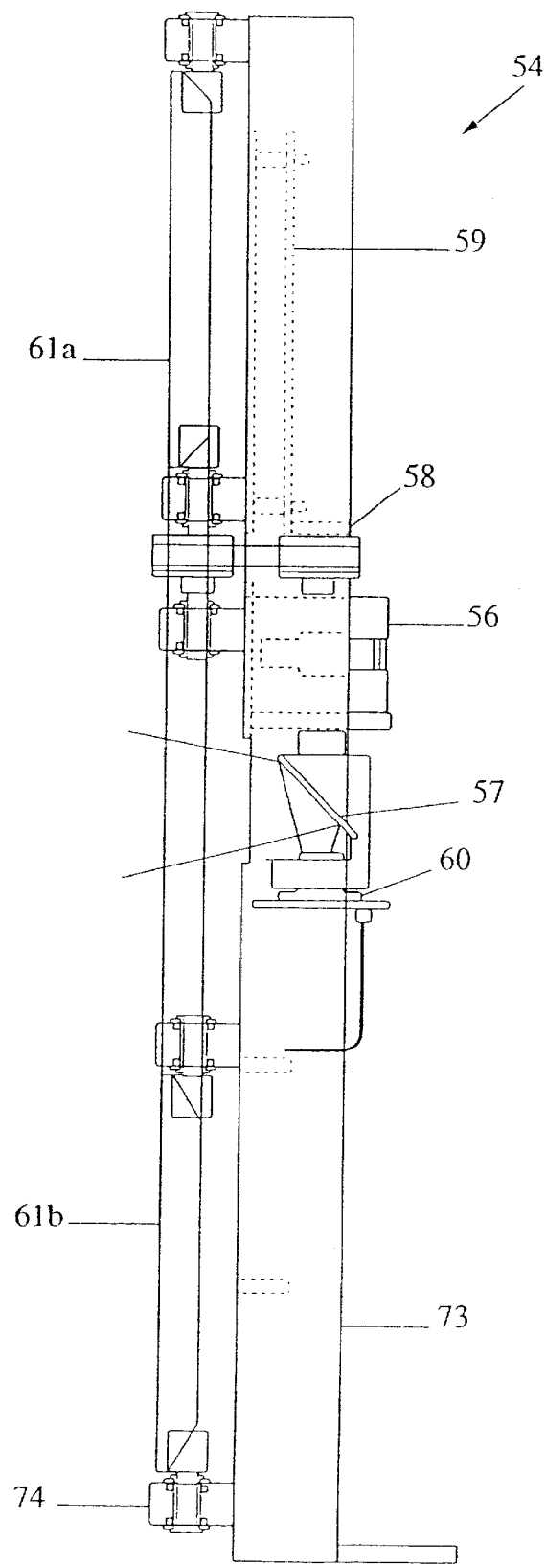
FIG. 2 shows an example of a tracking tower that corresponds to one embodiment of the present invention.
Figure 3:
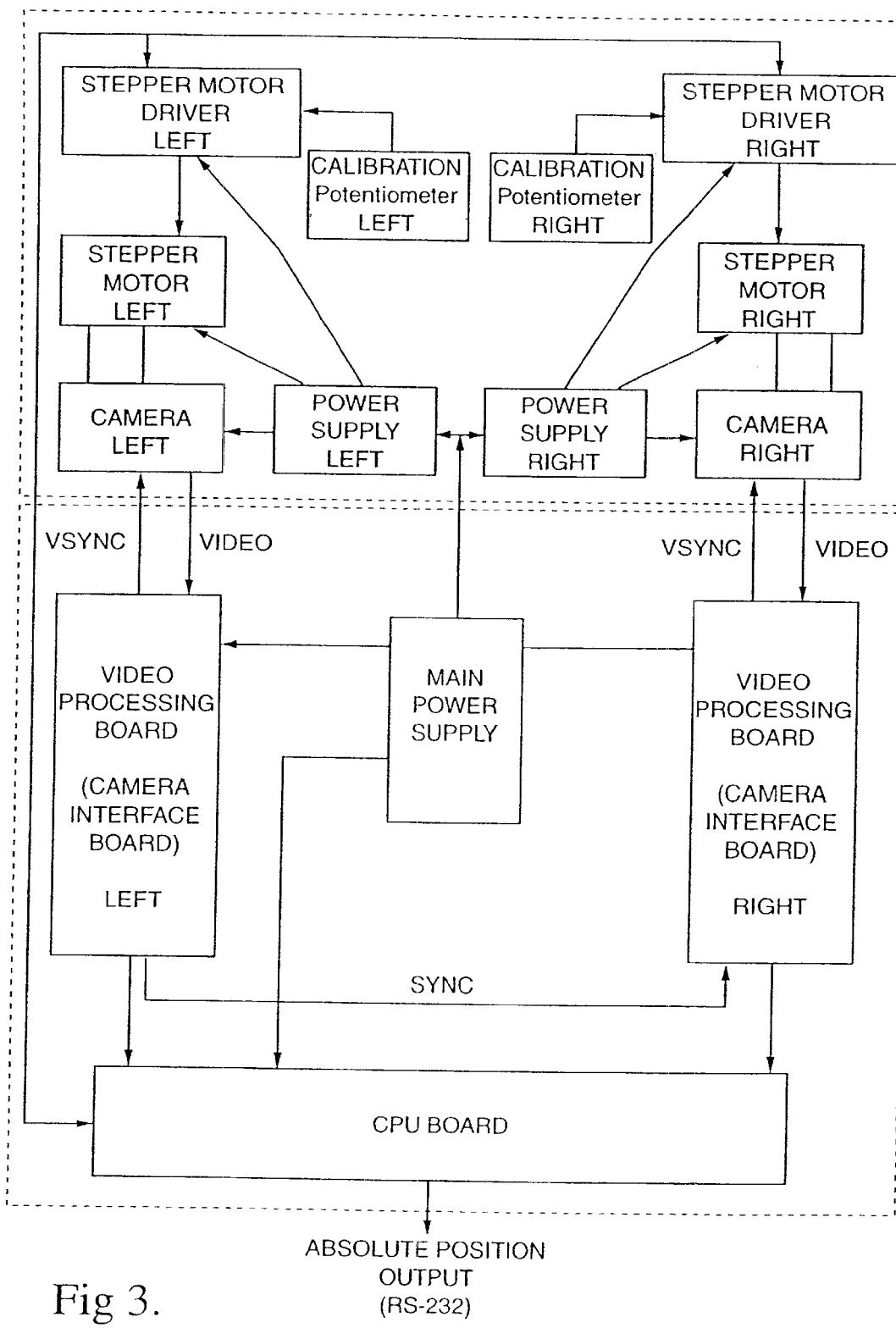
FIG. 3 shows a block diagram of the typical elements of the tracking towers (minus illuminating means) and processing means of one embodiment of the present invention.

As can be seen from FIGS. 1 and 2, in a preferred embodiment the present invention provides two tracking towers (54), one either side of the screen (70) and a processing means (55) located below the screen (70) in a base unit (72). The tracking towers (54) may be inclined towards the center of the screen (70) to ensure the area in front of the screen (70) is illuminated. Ideally, this angle of inclination is approximately 20°. Preferably, each tracking tower (54) contains a panning camera (60) for tracking the viewer's eyes. Such a Dual Pan Eye Tracking Apparatus may conveniently consist of two tracking towers (54) and a processor module (55). The tracking towers (54) can include a support frame (73), and an IR illumination carrier frame (74) with mounts and pivots. In the preferred embodiment, each tracking tower includes an upper illumination means (61a) and a lower illumination means (61b). Both the upper and lower illumination means (61a, 61b) may be formed by a bank of infra-red LED's all of which act to illuminate the viewer. Ideally, the, or each, illumination means is moveable and also generally tracks the viewer's head. The orientation of the illumination means (61) can be arranged as a result of feedback from the processing means (55). That is, the processing means (55) can be used to locate the viewer's eyes for an autostereoscopic display device, and also for adjustments to the illumination means (61) which assisted in the location of the viewer's eyes. This movement of the illumination means (61) has the advantage that sufficient light illuminates the viewer at all times thereby enabling the cameras (60) and processing means (55) to detect the viewer's eyes and/or head. Further, the use of directional illuminating means improves the ability of the system to meet IR safety regulations. A stronger, more focused, "beam" may be directed at the viewer, without the need to flood the entire area in infra-red. A feature which may be of particular relevance to any casual observers.

The towers (54) may also include a stepper motor or DC motor (56), a mirror (57), a position feed back device (58), that measures the angle through which the tower rotates and a power supply (59). This preferred layout is shown at FIG. 2. This shows a vertical axis pan unit with a front silvered mirror (57) at 45°. The inclusion of a mirror (57) in the tracking towers (54) allows for a more compact unit, which would be less obtrusive to the viewer, and require less real estate. The mirror (57) can be fixed with respect to the camera (60) or moveable. A fixed mirror decreases the amount of processing power required to determine the position of the viewer's eyes. However, a moveable mirror has the advantage of increasing the degree of freedom afforded to the viewer's movement. That is, a moveable mirror will enable a viewer to be tracked over a greater area than a fixed mirror.

The IR Tracking Camera (60) can be mounted so the axis of the stepper motor (56) is in the optical center of the camera lens, i.e., the camera is arranged to pivot about its optical center. The camera (60) revolves with the mirror unit (57) and remains in a relative axial position to the illumination arrays (61a, 61b). Aligning adjustments can be incorporated in the design to allow for initial set up and calibration adjustments. As an alternate to the stepper motor (56), a DC servomotor with a PID controller could provide the rotation drive for the camera and IR illumination arrays.

The processor unit (55) may consist of a Composite Video Image Processor for each camera (60) and a CPU Board. The processing of the video signal is ideally undertaken in hardware and software. Positional information of the eye location is constantly calculated in the CPU and the information used to drive the stepper motor (56) and hence the camera pan mechanism. The absolute position information of the center of reference between the eyes (as x, y and z coordinates) is also supplied as an output.

The processor unit (55) locates the position of the eyes by examining the video image. The processor examines the image from the video camera to determine the areas of the image that have high brightness levels. Since the viewers face is being illuminated with infrared light, then one of the highest levels of natural reflections or brightness levels from the face will be the reflection of the infrared light source from the cornea of the viewers eyes. The processor searches for these reflections on the basis that there are two eyes, that they are approximately 67 mm apart, and that they are located approximately horizontal to one another. After the eyes have been located initially, these attributes are used to verify that the bright features identified are in fact eyes and not other similar objects within the image.

There are two calibration sequences for this preferred embodiment. The first is a full set up calibration. The Flow Diagram of FIG. 4(a–c) details one embodiment of the calibration of the complete unit. A calibration frame is positioned in front of the complete unit. This frame consists of a series of IR LED's (the absolute position of each LED is known) on a horizontal and vertical axis, in the preferred embodiment the LED's are configured in the form of a cross. The z distance from the calibrations frame's LED's to the prescribed calibration datum point is also known. The operation of the LED's is controlled from the processor unit (55).

Figure 4A:
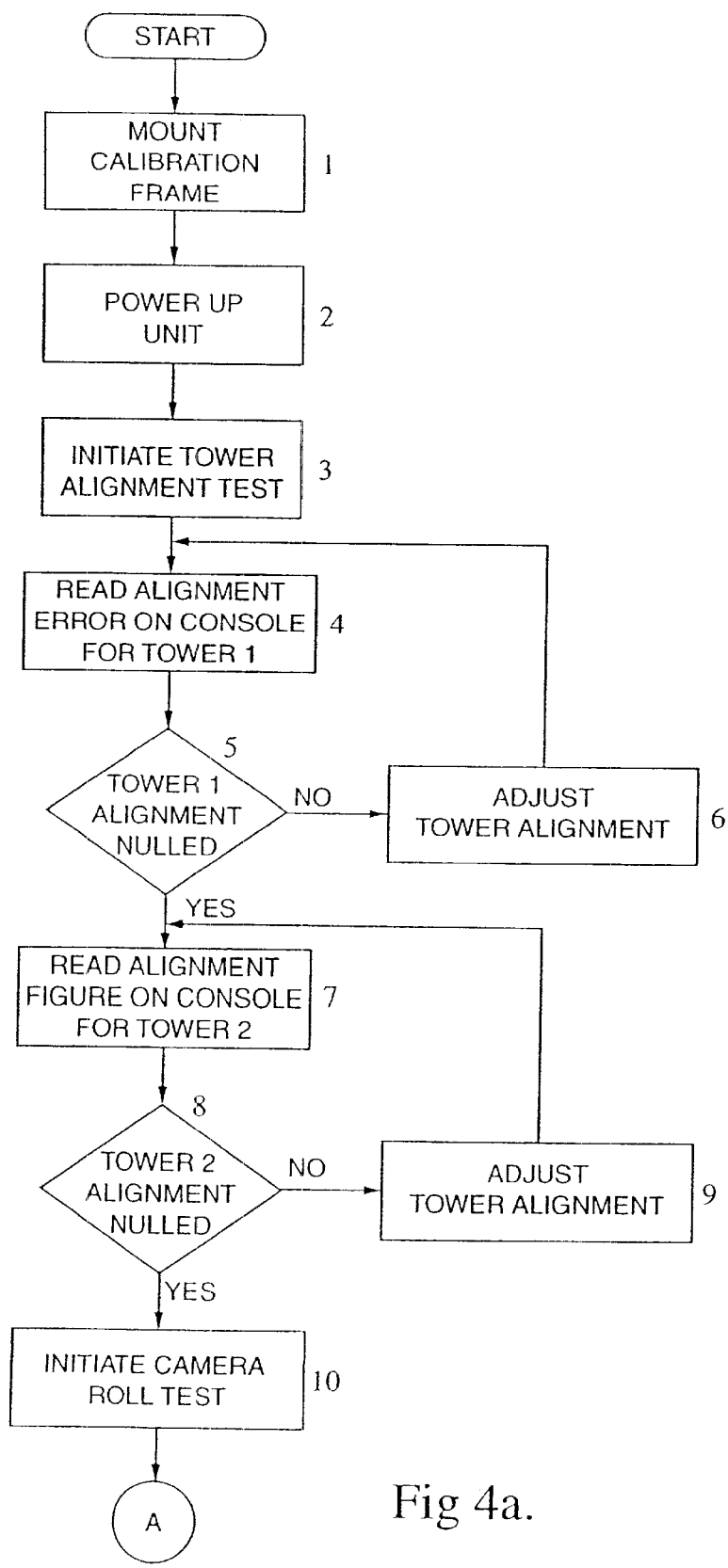
FIGS. 4a–c show a flow diagram of the calibration system of one embodiment of the present invention.
Figure 4B:
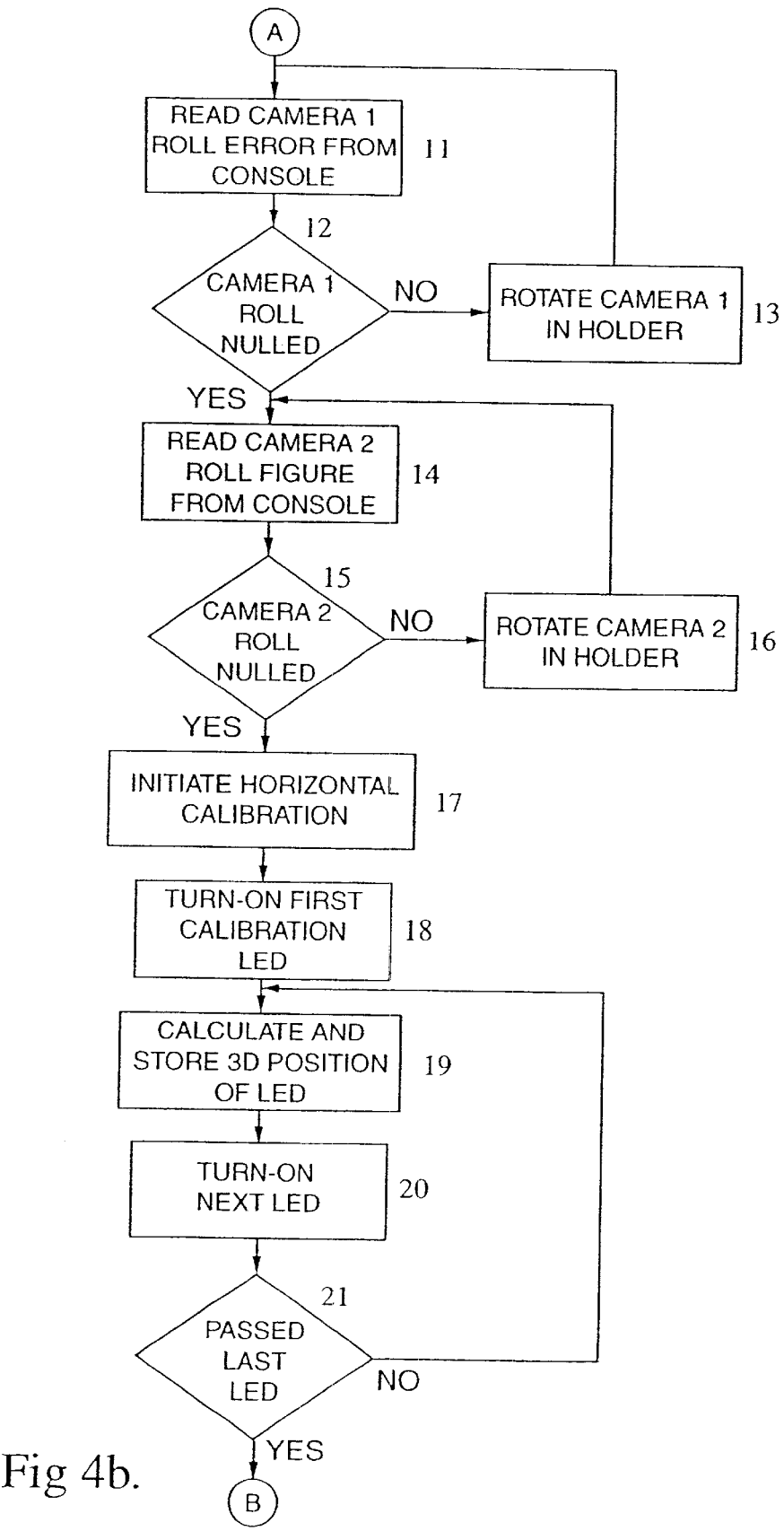
Figure 4C:
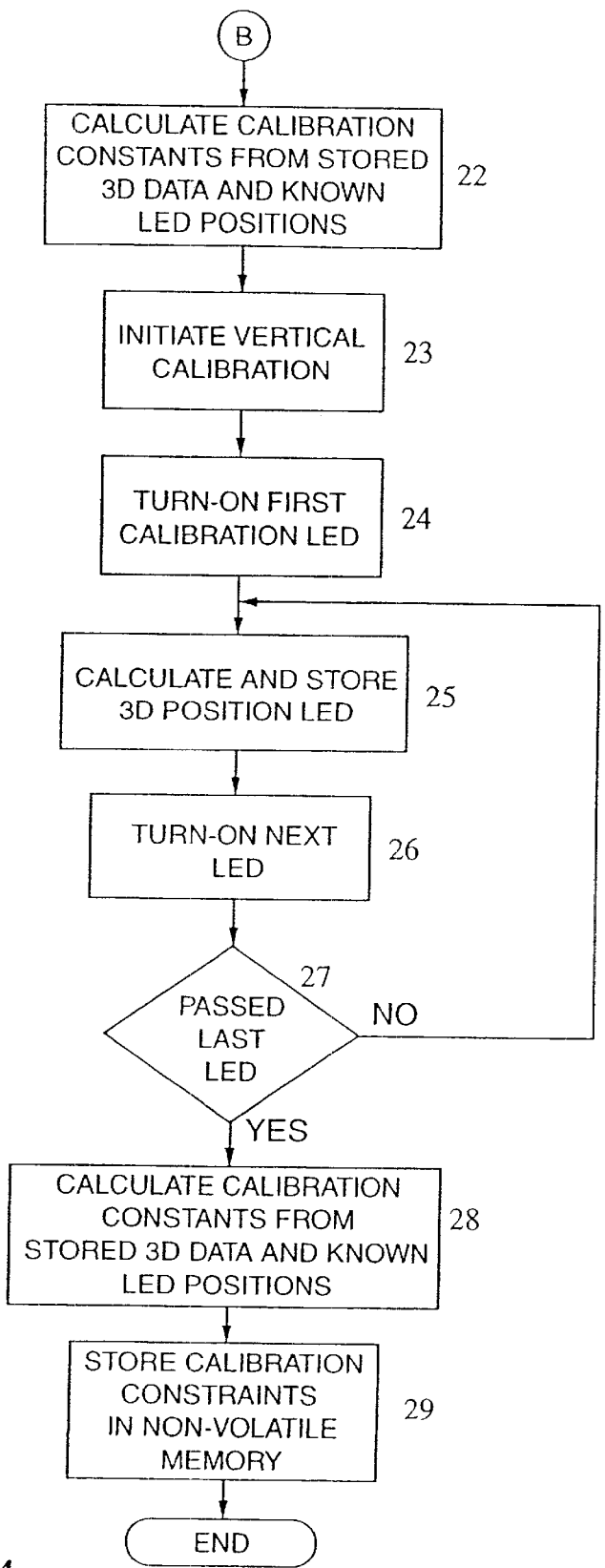

FIG. 4(a–c) details the operation of the calibration for this preferred embodiment. The calibration frame is mounted (1) at the calibration height and distance from the tracking towers (54). The calibration frame is powered up (2) by plugging into the processor unit (55) via a cable. Data is supplied via a monitor port on the processor unit (55). The first part of the calibration involves the alignment of the tracking towers (54), accordingly the tower alignment test (3) is initiated. The routine for adjusting the alignment of tower 1 is undertaken (4, 5 and 6) automatically on power up. This consists of moving the tower alignment until a nulled result is obtained. A similar routing is undertaken on tower 2, (7, 8 and 9) again until a nulled result is obtained. This completes the alignment calibration. Note: FIGS. 1 and 2 do not show alignment mechanism.

The next step is the camera roll adjustment. Roll adjustment compensates for the fact that the CCD element within the camera may not be mounted exactly horizontal within the camera mounting and compensates for the fact that in the preferred embodiment the camera is mounted pointing inwards and upwards towards the observer. Camera roll test is initiated (10) automatically on successful completion of the tower alignment routines. The routine for the rotational or roll alignment of camera 1 is undertaken (11, 12 and 13). This consists of rotating the camera in its mounting until a nulled result is obtained. A similar routine is undertaken on camera 2 (14, 15 and 16) again until a nulled result is obtained.

The next stage, horizontal calibration (17) is automatically initiated on successful completion of the camera roll calibration. This calibration routine is also an automatic process. The iterative routine (18, 19, 20 and 21) is performed on data processed from the two cameras. The calculated x, y and z position of each of the horizontal calibration LED's is stored. The absolute positions of the horizontal LED's are then used to calculate (22) the horizontal calibration constants for the system.

Vertical calibration (23) is carried out in a similar manner to the horizontal calibration (17). The iterative routine (24, 25, 26 and 27) is performed on data processed from the two cameras. The calculated x, y and z position of each of the vertical calibration LED's is stored. The absolute position of the vertical LED's are then used to calculate (28) the vertical calibration constants for the system.

The final calibration step is to store the calibration constants in nonvolatile memory (29).

The second calibration phase is an ongoing operational check calibration. This is related to the stepper motor drive system, where the step count is checked against the positional feed back device and corrected as required. This could be undertaken automatically with a DC servo motor with a PID control.

In an alternative embodiment, the illumination means is separated from the camera, in that they need not be located in the same tracking tower. This enables the illumination source to be located closer to the viewers face, thereby enabling the illumination means to have lower power usage, and reduced beam width, features which in an infra red environment assist in the system meeting the necessary health and safety standards. This embodiment also allows the camera(s) to be located further away from the viewer, and out of sight of the viewer if desired. Such cameras are also more likely to be able to employ a standard angle lens, as opposed to the likelihood of requiring cameras with wide angle lens, as the camera need not be located close to the viewer and illumination source.

The present invention may also be adapted to address one of the major problems associated with attempts to perform eye tracking, in the temporary loss of eye reflections associated with either blinking or looking away in another direction. To address this problem at least one further reference point for the eyes can be incorporated. This further reference point should only be achieved after eye lock (valid eye recognition) is confirmed. The method may be called associated head tracking and involves additional software routines. After the valid eye recognition is achieved, the system looks above the position of the eyes to find the edges of the head approximately in the position of the forehead. This is a transient point between the darkness of the background and the lighter face. One point on either side of the face can be established and the eye positions referenced to these points. If the eye lock is momentarily lost, the system can then continue to calculate the position of the eyes based on these reference points. Ideally, the position reference can be continually updated while eye lock is established if required.

Figure 5A:
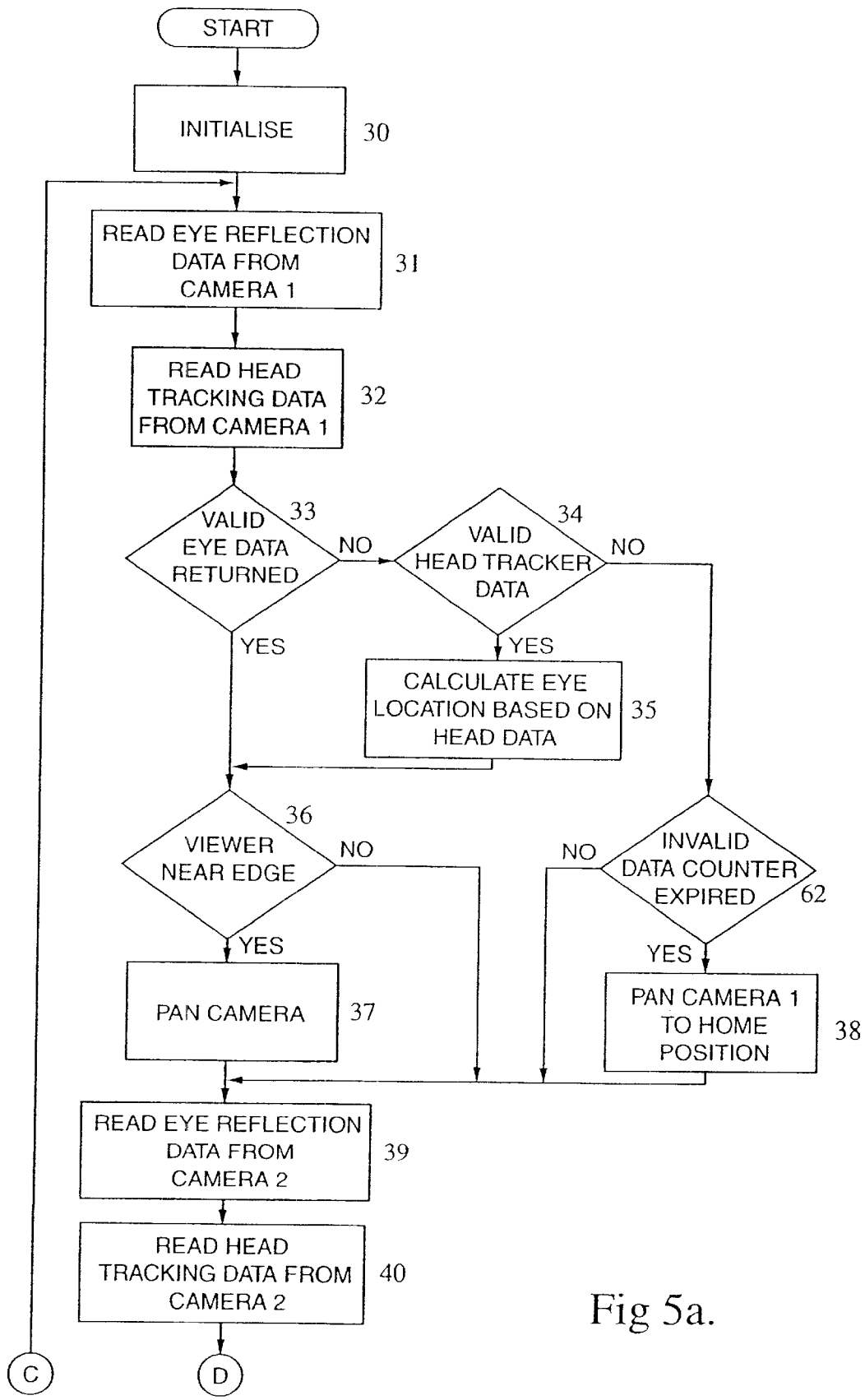
FIGS. 5a–b, show a flow diagram of the operation of the eye tracker and the head tracker in the preferred embodiment.
Figure 5B:
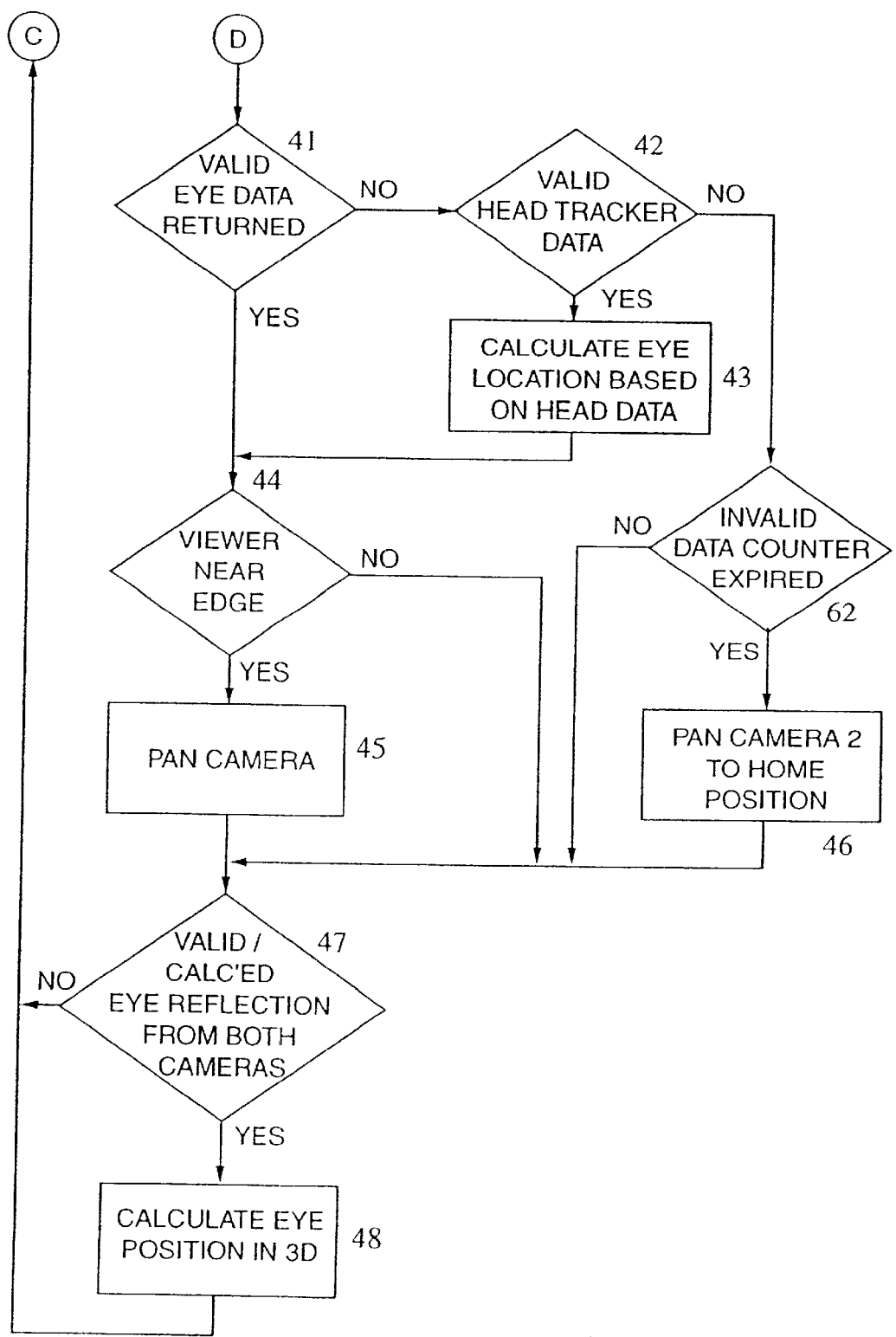

FIGS. 5a and 5b detail the operation of the eye tracking with head tracking system for this preferred embodiment of the invention. The system is initialized (30) automatically on power up. The operation of the system can be considered to be a continuous process to output a constant data stream for the absolute x, y and z positions of the observer's eyes. This is obtained by reading the eye reflection data from camera 1 (31) and reading the head tracking data from camera 1 (32). The eye reflection data is compared with the known characteristics of a valid eye reflection, in terms of shape and size etc, that are stored as parameters within the program. If the comparison does not indicate that a valid eye reflection has been located then the camera is panned to the home position after a predetermined time out period. Once a valid set of eye reflections have been established a referenced head position can be indexed to the eye position and will be retained as a valid head position (34). If subsequent valid eye data is not returned, due to blinking or closing the eyes, the head position is then used to calculate the eye position (35). If the valid eye position indicates the observer is near the horizontal limit of the field of view of the camera the stepper motor will be instructed to pan the camera (37) to centralize the image in the field of view. Whilst the embodiment described is predominately intended to track an observer as they move in the x axis, should the valid eye position indicate that the observer is near the vertical limit of the field of view then a tilt mechanism attached to the camera, or 45 degree mirror, would enable the tracking in this direction to also be extended.

The same process is used for camera 2 (39 to 46) as described for camera 1 (31 to 38). With valid and or calculated eye reflections from both cameras (47) the eye position in x, y and z can be calculated (48). If valid or calculated eye reflections are not available then no valid output can be calculated and the previous values for x, y and z are repeated until valid data updates the system. An invalid data counter (62) is in both the camera 1 and the camera 2 flow diagram. If the camera data continues to register invalid, the camera will pan to the home position.

Such a system can also be adapted to establish a stable position indication of the eyes even when the viewer is wearing glasses. The reflections from glasses are multiple and can be fast moving and unstable. Once the position of the glasses is established, the system looks for the transient from the dark background to the lighter face above the level of the glasses. As the viewer moves, looks down or right and left the reference points act as a filter, rejecting the invalid data and updating the reference when valid position data is processed.

The confinement of IR light to below the level of Class 1 IR Illumination Standards Requirement was considered a design criterion. Two methods were formulated to ensure the present invention provides a safe working environment. The first involved determining the minimum IR Illumination possible to obtain accurate and repeatable eye position data. This involved the incorporation of a low light (IR) camera together with the axial mounted IR Illumination. The stand by condition of the system assumes that the viewer will enter the home position in the first third of the z viewing distance. The IR illumination and shutter speed is optimized for this viewing distance. As the viewer moves back (increase in z) the shutter speed is dynamically decreased and the IR illumination time is increased. The second method involves viewers not being the primary viewer. With the IR illumination articulated coaxially with the camera and with the IR LED's having an emission cone of a 40° solid angle, any other observer is outside the influence of the IR illumination and therefore exposed to less than Class 1 IR illumination Standards.

The cameras are also synchronized to minimize the IR illumination on time and to improve the accuracy of the system.

Figure 6:
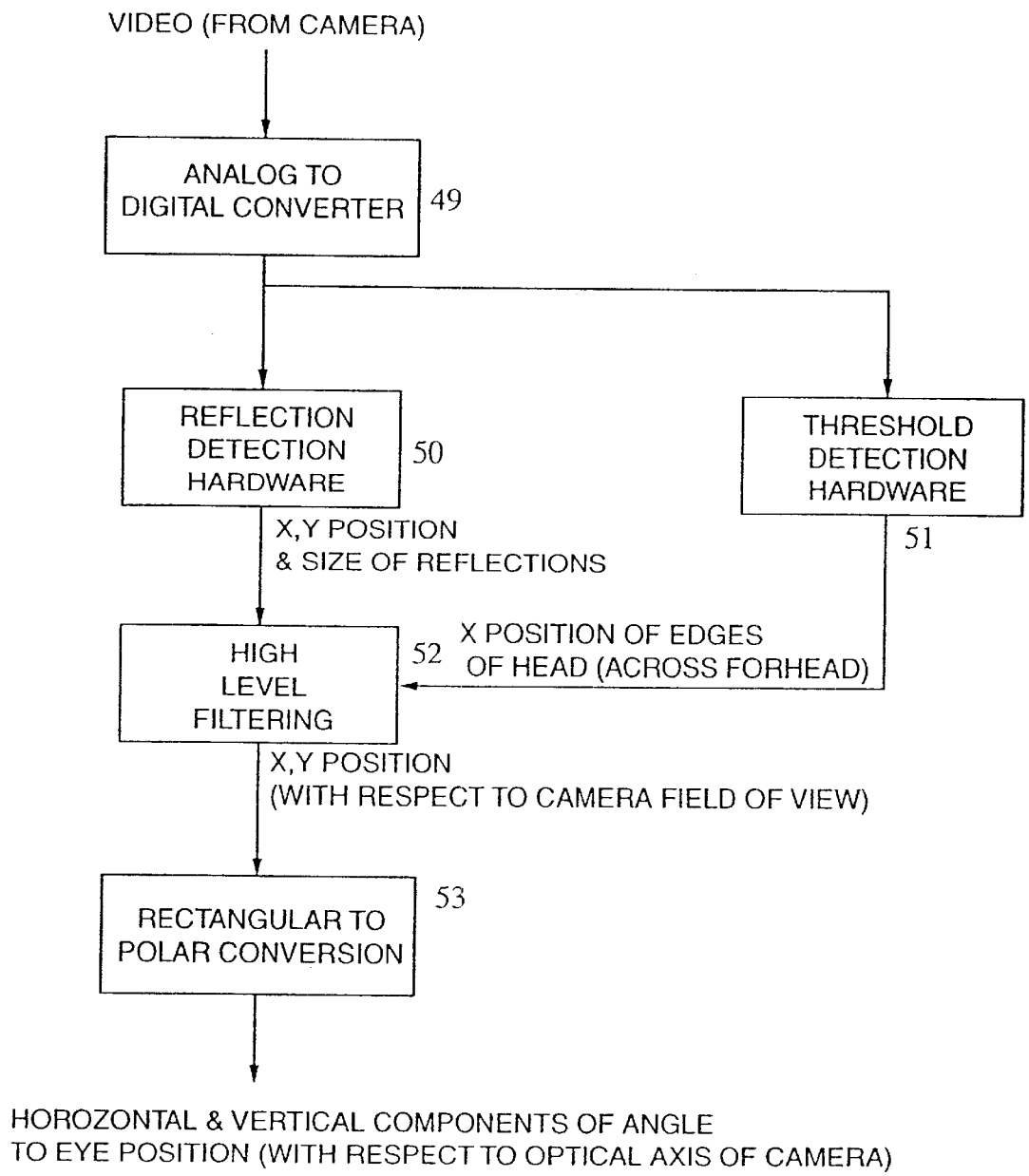
FIG. 6 shows a block diagram of hardware requirements for one embodiment of the present invention.

FIG. 6 details a typical block diagram of the hardware aspects of the operation for this preferred embodiment. Video from the camera(s) is converted from an analog to a digital signal (49). Hardware processes the digital data using transient reflection detection (50) and threshold detection (51) to obtain the x and y positions of the reflections and the x positions of the left and right edges of the observer's head (above the level of the detected eyes). High level filtering is used to establish the X and y position of the detected reflections with respect to the camera's field of view (52). The x and y rectangular positions are then converted to a polar coordinate position (53). That is the x and y position with respect to the camera field of view is converted to the horizontal and vertical components of angle to the eye position with respect to the optical axis of the camera. With this positional data from both cameras and the positional data from the pan position of the cameras the absolute location of the eyes in x, y and z space can be calculated. This data can be output from the system via a nominated data stream format in various serial communication modes or other methods familiar to those skilled in the art.

The present invention is of particular advantage to the Applicant's existing autostereoscopic display system, however, it is also of advantage to all other autostereoscopic display systems. The tracking system as disclosed herein allows the viewer additional freedom of movement not available in existing systems. Where previously the viewer was constrained to remain a relatively fixed distance from the display means, the present invention provides a system whereby the viewer can move away from, or towards, the screen without loss of stereoscopic effect. That is, the ability to track the viewer's eyes in the x, y and z directions enables the stereoscopic system to correctly project the left eye and right eye images for viewing by the viewer's respective left and right eyes.

Whilst the main advantage of the eye tracking unit of the present invention is that the viewer is not required to remain a fixed distance from the screen, the preferred embodiments of the present invention are also able to address other problems with existing systems which attempt to track a viewer's eyes in the x and y direction by being able to compensate for when valid eye data is not valid, or the viewer is wearing glasses. However, it will be understood that modifications and variations such as would be apparent to a skilled addressee are considered within the scope of the present invention.

What is claimed is:

1. An autostereoscopic display system comprising:
   a display means for displaying images to be viewed by a viewer;
   a tracking tower located on either side of the display means, each tracking tower including:
      an upper and lower illumination means for illuminating at least the eyes of a viewer;
      a vertically mounted camera for capturing at least the reflected light from the eyes of the viewer;
      a camera mounted perpendicular to the horizontal for capturing at least the reflected light from the eyes of the view; and
      a mirror positioned to enable the vertically mounted camera to capture images of the viewer in front of the tracking tower;
   a processing means for receiving the images captured by each camera, determining the position of the viewer's eyes, and sending the output from the processing means to each tracking tower to thereby adjust each said camera in response to movement of the viewer;
   and wherein the output from the processing means is utilized to display respective left and right eye images of the image to be viewed by the viewer on the display means.

2. The display system as claimed in claim 1, wherein said processing means is located below the display means.

3. The display system as claimed in claim 1, wherein output from the processing means is utilized to adjust the orientation of each illumination means in response to movement of the viewer.

4. The display system as claimed in claim 1, wherein each illumination means includes a bank of infra red LED's.

5. The display system as claimed in claim 1, wherein output from the processing means is utilized to adjust the orientation of each camera in response to movement of the viewer.

6. The display system as claimed in claim 1, wherein each camera is arranged to pivot about its optical center.

7. The display system as claimed in claim 1, wherein output from the processing means is utilized to adjust the orientation of each mirror in response to movement of the viewer.

8. The display system as claimed in claim 1, wherein said processing means utilizes a method of triangulation to assist in the location of the viewer's eyes.

9. An autostereoscopic display including the system as claimed in claim 8.

* * * * *